(12) United States Patent
Soares Da Silva et al.

(10) Patent No.: US 8,481,582 B2
(45) Date of Patent: Jul. 9, 2013

(54) 1,3-DIHYDROIMIDAZOLE-2-THIONE DERIVATIVES AS INHIBITORS OF DOPAMINE-BETA-HYDROXYLASE

(75) Inventors: Patrício Manuel Vieira Araújo Soares Da Silva, Oporto (PT); David Alexander Learmonth, Alfena (PT); Alexander Beliaev, Mindelo (PT)

(73) Assignee: Bial-Portela & CA, S.A., S. Mamede Do Coronado (PT)

( * ) Notice: Subject to any disclaimer, the term of this patent is extended or adjusted under 35 U.S.C. 154(b) by 535 days.

(21) Appl. No.: 12/599,014

(22) PCT Filed: May 6, 2008

(86) PCT No.: PCT/PT2008/000019
§ 371 (c)(1),
(2), (4) Date: Dec. 30, 2009

(87) PCT Pub. No.: WO2008/136695
PCT Pub. Date: Nov. 13, 2008

(65) Prior Publication Data
US 2010/0137390 A1    Jun. 3, 2010

(30) Foreign Application Priority Data
May 8, 2007    (GB) .................................. 0708818.0

(51) Int. Cl.
*A61K 31/4178*    (2006.01)
*C07D 207/48*    (2006.01)

(52) U.S. Cl.
USPC ........................................ 514/392; 548/311.4

(58) Field of Classification Search
USPC ........................................ 514/392; 548/311.4
See application file for complete search history.

(56) References Cited

U.S. PATENT DOCUMENTS
4,217,347 A * 8/1980 Horovitz et al. ........... 514/223.5

FOREIGN PATENT DOCUMENTS
| EP | 1408038 | * | 4/2004 |
| WO | 9529165 A2 | | 11/1995 |
| WO | 2004033447 A1 | | 4/2004 |
| WO | 2008136695 A1 | | 11/2008 |

OTHER PUBLICATIONS

Beliaev, Alexandre, et al., "Synthesis and Biological Evaluation of Novel, Peripherally Selective Chromanyl Imidazolethione-Based Inhibitors of Dopamine B-Hydroxylase," J. Med. Chem., 2006, vol. 49, pp. 1191-1197.
Benedict, Claude R., et al., "Prognostic Significance of Plasma Norepinephrine in Patients with Asymptomatic Left Ventricular Dysfunction," Circulation, 1996, vol. 94, No. 4, pp. 690-697.
Cohn, Jay N., et al., "Plasma Norepinephrine as a Guide to Prognosis in Patients with Chronic Congestive Heart Failure," The New England Journal of Medicine, 1984, vol. 311, No. 13, pp. 819-823.
Foreign communication from the priority application—International Preliminary Report on Patentability, PCT/PT2008/000019, Nov. 19, 2009, 7 pages.
Foreign communication from the priority application—International Search Report and Written Opinion, PCT/PT2008/000019, Sep. 3, 2008, 9 pages.
Goldstein, Menek, et al., "Inhibition of Dopamine-B-Hydroxylase by Disulfiram," Life Sciences, 1964, vol. 3, pp. 763-767, Pergamon Press, Inc.
Hasking, G.J., et al., "Norepinephrine spillover to plasma in patients with congestive heart failure: evidence of increased overall and cardiorenal sympathetic nervous activity," Circulation, 1986, vol. 73, No. 4, pp. 615-621.
Hidaka, Hiroyoshi, Fusaric (5-Butylpicolinic) Acid, an Inhibitor of Dopamine B-Hydroxylase, affects serotonin and noradrenaline, Nature, 1971, vol. 231, pp. 54-55.
Johnson, G. A., et al., "In Vivo Inhibition of Dopamine B-Hydroxylase by 1-Phenyl-3-(2-Thiazolyl)-2-Thiourea (U-14,624)," The Journal of Pharmacology and Experimental Therapeutics, 1970, vol. 171, No. 1, pp. 80-87.
Leimbach, Jr., W.N., et al., "Direct evidence from intraneural recordings for increased central sympathetic outflow in patients with heart failure," Circulation, 1986, vol. 73, No. 5, pp. 913-919.

(Continued)

*Primary Examiner* — Sreeni Padmanabhan
*Assistant Examiner* — Sahar Javanmard
(74) *Attorney, Agent, or Firm* — McCarter & English, LLP; Steven G. Davis; Wei Song

(57) ABSTRACT

Compounds of formula I and a method for their preparation are described:

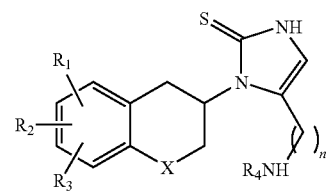

where $R_1$, $R_2$ and $R_3$ are the same or different and signify hydrogens, halogens, alkyl, nitro, amino, alkylcarbonylamino, alkylamino or dialkylamino group; $R_4$ signifies -alkyl-aryl or -alkyl-heteroaryl; X signifies $CH_2$, oxygen atom or sulphur atom; n is 2 or 3; including the individual (R)- and (S)-enantiomers or mixtures of enantiomers thereof; and including pharmaceutically acceptable salts and esters thereof. The compounds have potentially valuable pharmaceutical properties for the treatment of cardiovascular disorders such as hypertension and chronic heart failure.

9 Claims, 2 Drawing Sheets

OTHER PUBLICATIONS

Levine, T. Barry, et al., "Activity of the Sympathetic Nervous System and Renin-Angiotensin System Assessed by Plasma Hormone Levels and Their Relation to Hemodynamic Abnormalities in Congestive Heart Failure," The American Journal of Cardiology, May 1982, vol. 49, pp. 1659-1666.

Lippmann, W., et al., "Dopamine-B-Hydroxylase Inhibition by Dimethyldithiocarbamate and Related Compounds," Biochem. Pharmacol., 1969, vol. 18, pp. 2507-2516.

Parmley, William W., "Neuroendocrine Changes in Heart Failure and Their Clinical Relevance," Clin. Cardiol., 1995, vol. 18, pp. 440-445.

Pfeffer, Marc A., et al., "B-Adrenergic Blockers and Survival in Heart Failure," The New England Journal of Medicine, May 23, 1996, vol. 334, No. 21, pp. 1396-1397.

Stanley, William C., et al., "Catecholamine modulatory effects of nepicastat (RS-25560-197), a novel, potent and selective inhibitor of dopamine-B-Hydroxylase," British Journal of Pharmacology, 1997, vol. 121, pp. 1803-1809, Stockton Press.

American Psychiatric Association, "Diagnostic and Statistical Manual of Mental Disorders," Fourth Edition, Text Revision, 2000, pp. 429-484, American Psychiatric Association.

* cited by examiner

BIA 5-497

BIA 5-498

BIA 5-508

BIA 5-1058

Nepicastat

BIA 5-453

1,3-DIHYDROIMIDAZOLE-2-THIONE DERIVATIVES AS INHIBITORS OF DOPAMINE-BETA-HYDROXYLASE

CROSS-REFERENCE TO RELATED APPLICATIONS

This application is a filing under 35 U.S.C. 371 of International Application No. PCT/PT2008/000019 filed May 6, 2008, entitled "1,3-Dihydroimidazole-2-Thione Derivatives as Inhibitors of Dopamine-Beta-Hydroxylase," claiming priority of Great Britain Patent Application No. 0708818.0 filed May 8, 2007, which applications are incorporated by reference herein in their entirety.

FIELD OF THE INVENTION

This invention relates to peripherally-selective inhibitors of dopamine-β-hydroxylase, their method of preparation, and their use as a medicament.

BACKGROUND OF THE INVENTION

In recent years, interest in the development of inhibitors of dopamine-β-hydroxylase (DβH) has centred on the hypothesis that inhibition of this enzyme may provide significant clinical improvements in patients suffering from cardiovascular disorders such as hypertension or chronic heart failure. The rationale for the use of DβH inhibitors is based on their capacity to inhibit the biosynthesis of noradrenaline, which is achieved via enzymatic hydroxylation of dopamine. Activation of neurohumoral systems, chiefly the sympathetic nervous system, is the principal clinical manifestation of congestive heart failure (Parmley, W. W., Clinical Cardiology, 18: 440-445, 1995). Congestive heart failure patients have elevated concentrations of plasma noradrenaline (Levine, T. B. et al., Am. J. Cardiol., 49:1659-1666, 1982), increased central sympathetic outflow (Leimbach, W. N. et al., Circulation, 73: 913-919, 1986) and augmented cardiorenal noradrenaline spillover (Hasking, G. J. et al., Circulation, 73:615-621, 1966). Prolonged and excessive exposure of the myocardium to noradrenaline may lead to down-regulation of cardiac $\beta_1$-adrenoceptors, remodelling of the left ventricle, arrhythmias and necrosis, all of which can diminish the functional integrity of the heart. Congestive heart failure patients who have high plasma concentrations of noradrenaline also have the most unfavourable long-term prognosis (Cohn, J. N. et al., N. Engl. J. Med., 311:819-823, 1984). Of greater significance is the observation that plasma noradrenaline concentrations are already elevated in asymptomatic patients with no overt heart failure and can predict ensuing mortality and morbidity (Benedict, C. R. et al., Circulation, 94:690-697, 1996). An activated sympathetic drive is not therefore merely a clinical marker of congestive heart failure, but may contribute to progressive worsening of the disease.

Inhibition of sympathetic nerve function with adrenoceptor antagonists appeared a promising approach, however a significant proportion of patients do not tolerate the immediate haemodynamic deterioration that accompanies 13-blocker treatment (Pfeffer, M. A. et al., N. Engl. J. Med., 334:1396-7, 1996). An alternative strategy for directly modulating sympathetic nerve function is to reduce the biosynthesis of noradrenaline via inhibition of DβH, the enzyme responsible for conversion of dopamine to noradrenaline in sympathetic nerves. This approach has several advantages including gradual modulation as opposed to abrupt inhibition of the sympathetic system, and increased release of dopamine, which can improve renal function such as renal vasodilation, diuresis and natriuresis. Therefore, inhibitors of DβH may provide significant advantages over conventional β-blockers.

Several inhibitors of DβH have been thus far reported in the literature. Early first and second generation examples such as disulfuram (Goldstein, M. et al., Life Sci., 3:763, 1964) and diethyldithiocarbamate (Lippmann, W. et al., Biochem. Pharmacol., 18: 2507, 1969) or fusaric acid (Hidaka, H. Nature, 231, 1971) and aromatic or alkyl thioureas (Johnson, G. A. et al, J. Pharmacol. Exp. Ther., 171: 80, 1970) were found to be of low potency, exhibited poor selectivity for DβH and caused toxic side effects. The third generation of DβH inhibitors however, were found to have much greater potency, such as for example, nepicastat (RS-25560-197, $IC_{50}$ 9 nM) (Stanley, W. C., et al., Br. J. Pharmacol., 121: 1803-1809, 1997), which was developed to early clinical trials. Although devoid of some of the problems associated with first and second generation DβH inhibitors, a very important discovery was that nepicastat was found to cross the blood brain barrier (BBB), and was thereby able to cause central as well as peripheral effects, a situation which could lead to undesired and potentially serious CNS side-effects of the drug. Therefore, there remains an unfulfilled clinical requirement for a potent, non-toxic and peripherally selective inhibitor of DβH, which could be used for treatment of certain cardiovascular disorders. A DβH inhibitor with similar or even greater potency than nepicastat, but devoid of CNS effects (inability to cross the BBB) would provide a significant improvement over all DβH inhibitor compounds thus far described in the prior art.

Dopamine-β-hydroxylase inhibitors are also disclosed in WO95/29165. Furthermore, WO 2004/033447 discloses dopamine-β-hydroxylase inhibitors having high potency and significantly reduced brain access, giving rise to potent and peripherally selective DβH inhibitors.

SUMMARY OF THE INVENTION

We have now found new compounds which are potent dopamine-β-hydroxylase inhibitors having high potency and significantly reduced brain access.

BRIEF DESCRIPTION OF THE DRAWINGS

Reference is now made to the accompanying drawings, in which.

DETAILED DESCRIPTION OF THE INVENTION

Figure 1:
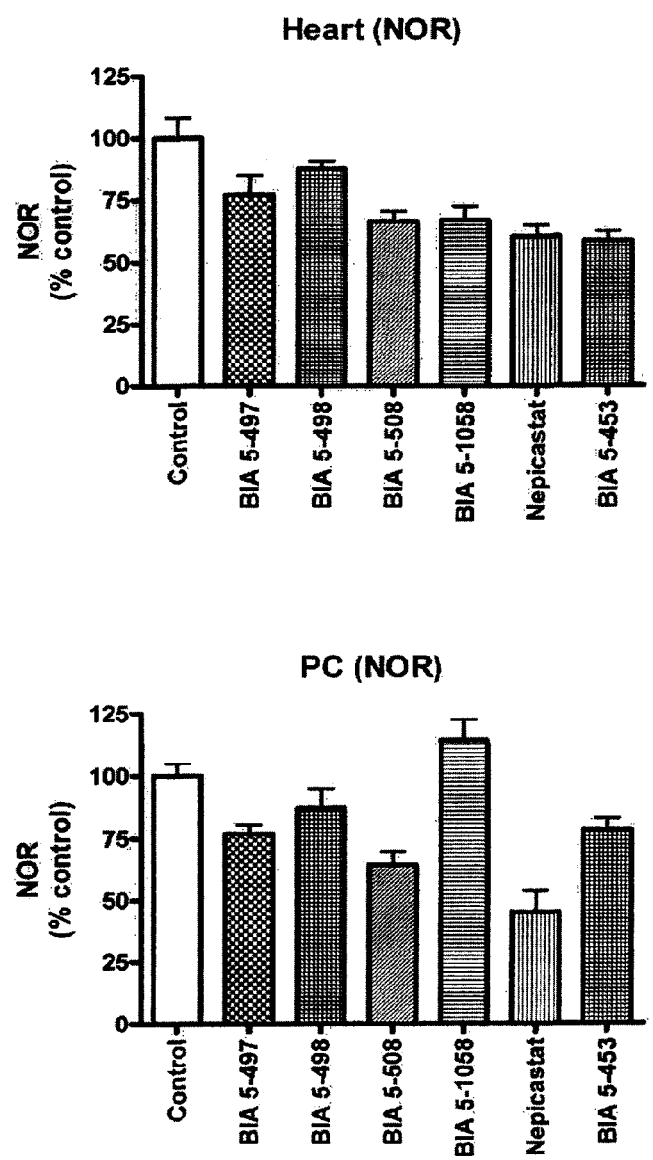
FIG. 1 shows the effect of the compounds tested on noradrenaline levels in the heart and parietal cortex.

According to one aspect of the invention, there is provided a compound of formula I:

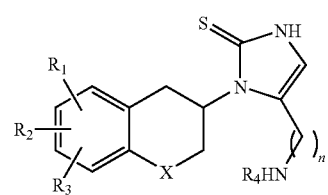

where $R_1$, $R_2$ and $R_3$ are the same or different and signify hydrogens, halogens, alkyl, nitro, amino, alkylcarbonylamino, alkylamino or dialkylamino group; $R_4$ signifies -alkylaryl or -alkylheteroaryl; X signifies $CH_2$, oxygen atom or sulphur atom; n is 2 or 3; including the individual (R)- and (S)-enantiomers or mixtures of enantiomers thereof; and including pharmaceutically acceptable salts and esters thereof, wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyl, alkyloxy, halogen or nitro group; the term halogen means fluorine, chlorine, bromine or iodine; the term heteroaryl means heteroaromatic group.

In a preferred embodiment n=2.

In a further preferred embodiment, X=O.

Preferably $R_4$ signifies —$CH_2$-aryl or —$CH_2$-heteroaryl.

In one embodiment, the aryl group of $R_4$ is unsubstituted.

The aryl group of $R_4$ may preferably be phenyl.

Desirably, one of $R_1$, $R_2$ and $R_3$ is hydrogen, and the others are fluorine.

The compound of formula I may be provided as the (R) or (S) enantiomer, or as a mixture of the (R) and (S) enantiomers in any proportions, including the racemate. The compound of formula I most preferably consists of the R-enantiomer.

The compound may suitably be provided in the form of the hydrochloride salt. However, given the secondary aliphatic amino group, it will be obvious to the skilled technician that other acid salts can be made and are within the scope of the claimed invention.

According to another aspect of the invention, there is provided a process for the preparation of the individual (R)- and (S)-enantiomers or mixtures of enantiomers, and pharmaceutically acceptable salts of a compound of formula I as described above, which comprises reacting the individual (R)- or (S)-enantiomers or mixtures of enantiomers of a compound of formula III:

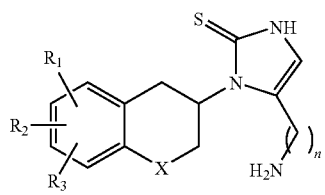

III where X, $R_1$, $R_2$, $R_3$ and n have the same meaning as defined for formula I above, with a compound of formula IV:

IV where $R_5$ signifies aryl or heteroaryl, wherein the term aryl means a phenyl or naphthyl group, optionally substituted by alkyl, alkyloxy, halogen or nitro group; the term halogen means fluorine, chlorine, bromine or iodine; the term heteryl means heteroaromatic group; under reductive alkylation conditions.

The conditions necessary for the above reductive alkylation will be apparent to those skilled in the art.

According to a particularly advantageous embodiment of the invention there is provided a compound of formula X:

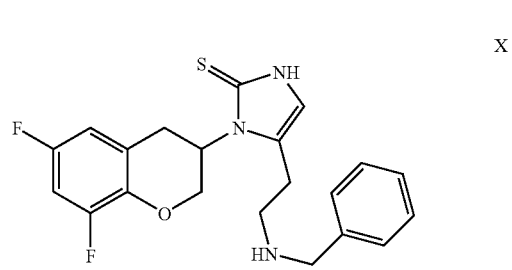 [SMILES: Fc1cc(F)c2c(c1)CC(n1c(CCNCc3ccccc3)c[nH]c1=S)CO2]

X its (R) or (S) enantiomer, or mixture of (R) and (S) enantiomer, or pharmaceutically acceptable salts or esters thereof.

The compound of formula X may be provided as the (R) or (S) enantiomer, or as a mixture of the (R) and (S) enantiomers in any proportions, including the racemate. Preferably, the compound of formula X is provided as the R-enantiomer, (R)—X:

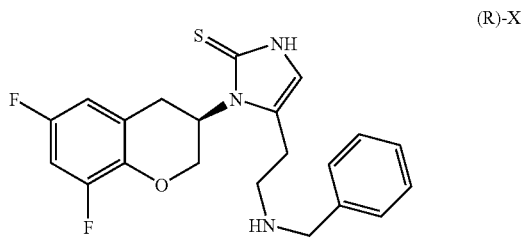 [SMILES: Fc1cc(F)c2c(c1)C[C@@H](n1c(CCNCc3ccccc3)c[nH]c1=S)CO2]

(R)-X

The compound of formula X (or R—(X)) is suitably provided as the hydrochloride salt. However, given the secondary aliphatic amino group, it will be obvious to the skilled technician that other acid salts can be made and are within the scope of the claimed invention.

The compound of formula X may be prepared, for example, by reductive alkylation by treating, (R)-5-(2-aminoethyl)-1-(6,8-difluoro-chroman-3-yl)-1,3-dihydroimidazole-2-thione and benzaldehyde in a solvent or mixture of solvents, such as for example, methanol and dichloromethane, in the presence of a reducing reagent, such as for example, sodium cyanoborohydride, sodium triacetoxyborohydride, sodium borohydride and the like, or hydrogen in the presence of a hydrogenation catalyst. If preferred, after work-up the crude product may be purified by column chromatography on silica gel.

According to another aspect of the invention, there is provided a pharmaceutical composition comprising a therapeutically effective amount of a compound as described above in combination with a pharmaceutically effective carrier.

According to a further aspect of the invention, there is provided a composition comprising a therapeutically effective amount of a compound as described above in combination with a pharmaceutically effective carrier and one or more of the compounds selected from the classes described below.

In particular, the compounds of formula I or X may be combined with one or more of the following classes of compounds: diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; AT1 receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; and CNS acting agents.

The most useful diuretics include:
(1) Loop diuretics, in particular, furosemide, bumetanide, ethacrynic acid, torasemide, azosemide, muzolimine, piretanide, tripamide.
(2) Thiazide diuretics, in particular, bendroflumethiazole, chlorothiazide, hydrochlorothiazide, hydroflumethiazide, methylclothiazide, polythiazide, trichlormethiazide.
(3) Thiazide-like diuretics, in particular, chlorthalidone, indapamide, metozalone, quinethazone.
(4) Potassium sparing diuretics, in particular, amiloride, triamterene.
(5) Aldosterone antagonists, in particular, spirolactone, canrenone, eplerenone.
(6) Combinations of the above described diuretics.

More than one of the aforementioned diuretics may be used.

The most useful beta-adrenergic antagonists include: timolol, metoprolol, atenolol, propranolol, bisoprolol, nebivolol. More than one of the aforementioned beta-adrenergic antagonists may be used.

The most useful alpha2-adrenergic agonists include: clonidine, guanabenz, guanfacine. More than one of the aforementioned alpha2-adrenergic agonists may be used.

The most useful alpha1-adrenergic antagonists include: prazosin, doxazosin, phentolamine. More than one of the aforementioned alpha1-adrenergic antagonists may be used.

The most useful dual beta- and alpha-adrenergic antagonists (other than those mentioned elsewhere in the specification) include: carvedilol, labetalol. More than one of the aforementioned dual beta- and alpha-adrenergic antagonists may be used.

Potassium channel activators include nicorandil.

The most useful calcium channel blockers include: amlodipine, bepridil, diltiazem, felodipine, isradipine, nicardipine, nifedipine, nimodipine, nisoldipine, verapamil. More than one of the aforementioned calcium channel blockers may be used.

Anti-arrhythmics other than those mentioned elsewhere in the specification include: sodium channel blockers such as quinidine, procainamide, disopyramide, lidocaine, mexiletine, tocainide, phenyloin, encainide, flecainide, moricizine, and propafenone; potassium channel blockers such as: amiodarone, bretylium, ibutilide, dofetilide, azimilide, clofilium, tedisamil, sematilide, sotalol; and esmolol, propranolol, metoprolol. More than one of the anti-arrhythmics mentioned in the specification may be used.

The most useful ACE inhibitors include: benzepril, captopril, enalapril, fosinopril, lisinopril, imidapril, moexipril, perindopril, quinapril, ramipril, trandolapril. More than one of the aforementioned ACE inhibitors may be used.

The most useful AT1 receptor antagonists include: candesartan, irbesartan, losartan, telmisartan, valsartan, eprosartan. More than one of the aforementioned AT1 receptor antagonists may be used.

Lipid lowerers include: statins such as atorvastatin, cerivastatin, fluvastatin, lovastatin, mevastatin, pitavastatin, pravastatin, rosuvastatin, simvastatin; bile acid sequestrants such as cholestyramine, colestipol and colesevelam; cholesterol absorption inhibitors such as ezetimibe; fibrates such as fenofibrate, gemfibrozil; niacin. More than one of the aforementioned lipid lowerers may be used.

The most useful nitrates include organic nitrates such as: amyl nitrite, nitroglycerin, isosorbide dinitrate, isosorbide-5-mononitrate, erythrityl tetranitrate. More than one of the aforementioned organic nitrates may be used.

Endothelin antagonists include: bosentan, sitaxsentan. More than one of the aforementioned endothelin antagonists may be used.

The most useful vasodilators (other than those mentioned elsewhere in the specification) include: hydralazine, minoxidil, sodium nitroprusside, diazoxide. More than one of the aforementioned vasodilators may be used.

The most useful phosphodiesterase inhibitors include: milrinone, inamrinone. More than one of the aforementioned phosphodiesterase inhibitors may be used.

Cardiac glycosides include: allocar, corramedan, digitoxin, digoxin, lanoxin, purgoxin, cedilanid-D, crystodigin, lanoxicaps. More than one of the aforementioned cardiac glycosides may be used.

Serotonin antagonists include: clozapine, loxapine, olanzapine, risperidone, ziprasidone, ritanserin, ketanserin, amoxapine. More than one of the aforementioned serotonin antagonists may be used.

CNS acting agents other than those already mentioned elsewhere in this specification include imidazoline agonists such as moxonidine. The most useful CNS acting agent is methyldopa.

The most useful renin inhibitors include: aliskiren, enalkiren, ditekiren, terlakiren, remikiren, zankiren, ciprokiren. More than one of the aforementioned renin inhibitors may be used.

The most useful vasopeptidase inhibitors include: omapatrilat, sampatrilat, gemopatrilat. More than one of the aforementioned vasopeptidase inhibitors may be used.

Other pharmaceuticals used in treating heart failure may also be combined with the compounds of formula I or X. These include calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endotheliin-converting enzyme (NEP/ECE) inhibitors; nociceptin receptor (ORL-1) agonists (e.g. alprazolam); xanthine oxidase inhibitors; benzodiazepine agonists; cardiac myosin activators; chymase inhibitors; endothelial nitric oxide synthase (ENOS) transcription enhancers; neutral endopeptidase inhibitors such as thiorphan.

The invention also envisages the use of nepicastat with the classes of compounds described above.

For the preparation of pharmaceutical compositions of compounds of formula I or X, inert pharmaceutically acceptable carriers are admixed with the active compounds. The pharmaceutically acceptable carriers may be either solid or liquid. Solid form preparations include powders, tablets, dispersible granules and capsules. A carrier can be one or more substances which may also act as diluents, flavouring agents, solubilizers, lubricants, suspending agents, binders or tablet disintegrating agents; it may also be an encapsulating material.

Preferably, the pharmaceutical preparation is in unit dosage form, e.g. packaged preparation, the package containing discrete quantities of preparation such as packeted tablets, capsules and powders in vials or ampoules.

The dosages may be varied depending on the requirement of the patient, the severity of the disease and the particular compound being employed. For convenience, the total daily dosage may be divided and administered in portions throughout the day. It is expected that once or twice per day administration will be most suitable. Determination of the proper dosage for a particular situation is within the skill of those in the medical art.

According to another aspect of the invention, there is provided a compound of formula I or formula X as described above, for use as a medicament.

According to another aspect of the invention, there is provided the use of a compound of formula I or formula X as described above, in the manufacture of a medicament for treating disorders where a reduction in the hydroxylation of dopamine to noradrenaline is of therapeutic benefit.

The compounds of formula I or X may also be used in conjunction with one of more compounds selected form the following classes of compounds:
diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; AT1 receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; CNS acting agents; calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endotheliin-converting enzyme (NEP/ECE) inhibitors; nociceptin receptor (ORL-1) agonists (e.g. alprazolam); xanthine oxidase inhibitors; benzodiazepine agonists; cardiac myosin activators; chymase inhibitors; endothelial nitric oxide synthase (ENOS) transcription enhancers; and neutral endopeptidase inhibitors such as thiorphan.

As used herein, the term treatment and variations such as 'treat' or 'treating' refer to any regime that can benefit a human or non-human animal. The treatment may be in respect of an existing condition or may be prophylactic (preventative treatment). Treatment may include curative, alleviation or prophylactic effects. Treatment with a compound of formula I or X in combination with one of the other classes of compounds includes simultaneous and sequential administration of the two or more drugs.

According to another aspect of the invention, there is provided the use of a compound of formula I or formula X as described above, in the manufacture of a medicament for treating a subject afflicted by an anxiety disorder.

Anxiety disorders include but are not restricted to generalized anxiety disorders, social anxiety disorders, post-traumatic stress disorder, acute distress disorder, obsessive compulsive disorders, panic disorders such as panic attacks, and phobias such as agoraphobia, social phobias, specific phobias. Further anxiety disorders treatable using compounds of the present invention may be found in on pages 429-484 of American Psychiatric Association: *Diagnostic and Statistic Manual of Mental Disorders*, 4$^{th}$ edition, Text Revision, Washington, D.C., American Psychiatric Association, 2000.

According to another aspect of the invention, there is provided the use of a compound of formula I or formula X as described above, in the manufacture of a medicament for treating migraine.

According to another aspect of the invention, there is provided the use of a compound of formula I or formula X as described above, in the manufacture of a medicament for treating a subject afflicted by a cardiovascular disorder.

According to another aspect of the invention, there is provided the use of a compound of formula I or formula X as described above, in the manufacture of a medicament for treating hypertension, or chronic or congestive heart failure.

According to another aspect of the invention, there is provided the use of a compound of formula I or formula X as described above, in the manufacture of a medicament for treating one or more of the following indications: angina, arrhythmias, and circulatory disorders such as Raynaud's phenomenon.

According to another aspect of the invention, there is provided the use of a compound of formula I or formula X as described above, in the manufacture of a medicament for use in inhibiting dopamine-β-hydroxylase.

According to another aspect of the invention, there is provided a method of treating anxiety disorders comprising administering a therapeutically effective amount of a compound of formula I or formula X as described above to a patient in need thereof.

According to another aspect of the invention, there is provided a method of treating migraine comprising administering a therapeutically effective amount of a compound of formula I or formula X as described above to a patient in need thereof.

According to another aspect of the invention, there is provided a method of treating cardiovascular disorders comprising administering a therapeutically effective amount of a compound of formula I or formula X as described above to a patient in need thereof.

According to another aspect of the invention, there is provided a method of treating hypertension comprising administering a therapeutically effective amount of a compound of formula I or formula X as described above to a patient in need thereof.

According to another aspect of the invention, there is provided a method of treating chronic or congestive heart failure comprising administering a therapeutically effective amount of a compound of formula I or formula X as described above to a patient in need thereof.

According to another aspect of the invention, there is provided a method of treating one or more of the following indications: angina, arrhythmias, and circulatory disorders such as Raynaud's phenomenon, comprising administering a therapeutically effective amount of a compound of formula I or formula X as described above to a patient in need thereof.

The above-described methods of treatment may further comprise simultaneous or sequential administration of a drug from one of the following classes of compounds: diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; AT1 receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; CNS acting agents; calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endotheliin-converting enzyme (NEP/ECE) inhibitors; nociceptin receptor (ORL-1) agonists (e.g. alprazolam); xanthine oxidase inhibitors; benzodiazepine agonists; cardiac myosin activators;

chymase inhibitors; endothelial nitric oxide synthase (ENOS) transcription enhancers; and neutral endopeptidase inhibitors such as thiorphan.

Unless stated otherwise, in this specification the term alkyl (whether used on its own or used in combination with other moieties) means hydrocarbon chains, straight or branched, containing from one to six carbon atoms, optionally substituted by aryl, alkoxy, halogen, alkoxycarbonyl or hydroxycarbonyl groups; the term aryl (whether used on its own or used in combination with other moieties) means a phenyl or naphthyl group, optionally substituted by alkyl, alkyloxy, halogen or nitro group; and the term halogen means fluorine, chlorine, bromine or iodine; the term heteroaryl means heteroaromatic group. Moreover, the terms 'alkoxy' and 'alkyloxy' are interchangeable, unless indicated otherwise.

Materials and Methods

Male NMRI mice were obtained from Harlan-Interfauna (Spain) and were kept 10 per cage under controlled environmental conditions (12 h light/dark cycle and room temperature 22±1° C.). Food and tap water were allowed ad libitum and experimentation was performed during daylight hours.

Figure 2:
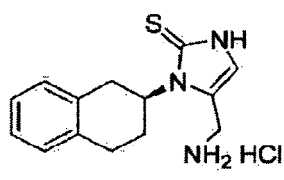
FIG. 2 shows the structures of the compounds tested.
Figure 2:
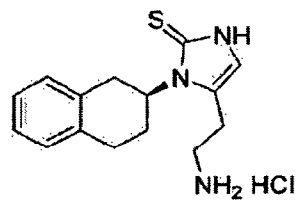
Figure 2:
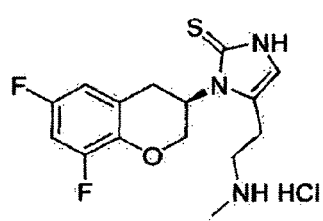
Figure 2:
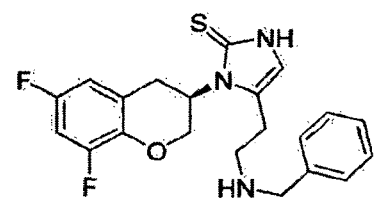
Figure 2:
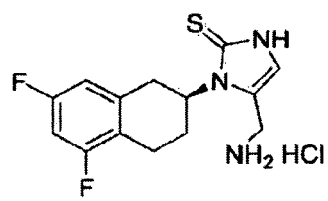
Figure 2:
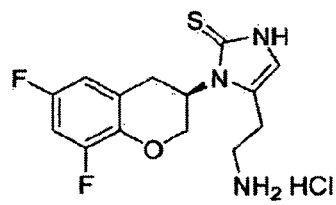

At time=0 h, animals were administered with either test compounds (see FIG. 2) at a given dose or vehicle (water) delivered orally via gavage. At 9 h post dose, the animals were sacrificed by decapitation and heart (left atrium and left ventricle) and brain (parietal cortex) were isolated, weighed and stored in a volume of 0.2 M perchloric acid for 12 h at 4° C. in the dark. Post incubation, the resulting supernatants were collected by centrifuge filtration of incubates (0.2 μM/10 min/~5000 rpm, 4° C.). Supernatants were stored frozen at −80° C. until analysis. Quantification of dopamine and noradrenaline in supernatants was performed by high pressure liquid chromatography with electrochemical detection.

Results

As can be seen from FIG. 1, the compound of formula X showed a marked selectivity for the heart compared to the brain, when compared with other DβH inhibitors of the prior art.

EXAMPLE

Example 1

(R)-5-(2-(benzylamino)ethyl)-1-(6,8-difluorochroman-3-yl)-1H-imidazole-2(3H)-thione To (R)-5-(2-aminoethyl)-1-(6,8-difluorochroman-3-yl)-1,3-dihydroimidazole-2-thione (2.36 g, 7.58 mmol) and benzaldehyde (0.85 ml, 8.34 mmol) in a mixture of methanol (15 ml), and dichloromethane (15 ml) sodium cyanoborohydride (0.67 g, 10.66 mmol) was added at 20-25° C. in portions. The mixture was stirred for 64 h, quenched with 1N HCl (12 ml) with stirring followed by 3N NaOH (12 ml). The mixture was extracted with DCM (100 ml), the organic phase was washed with brine (50 ml), dried (MgSO$_4$) and evaporated to dryness. The residue was purified on a silica gel column with ethyl acetate and a mixture of ethyl acetate with methanol (9:1) as eluents. Fractions containing the product were collected, evaporated under reduced pressure to approx 20 ml then cooled on ice. The precipitate was collected, washed with ethyl acetate—petroleum ether (1:1) mixture, dried on air. Yield was 1.25 g (41%), the product having a mp 188-90° C. (2-propanol-DCM).

It will be appreciated that the invention described above may be modified within the scope of the attached claims.

The invention claimed is:

1. A compound of formula X:

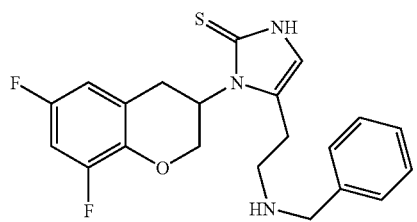

its (R) or (S) enantiomer, or mixture of (R) and (S) enantiomer, or a pharmaceutically acceptable salt thereof.

2. The compound according to claim 1, wherein the compound is the (R) enantiomer of the compound of formula X.

3. The compound according to claim 1, wherein the compound is the hydrochloride salt of the compound of formula X.

4. A pharmaceutical composition comprising a therapeutically effective amount of a compound according to claim 1, in combination with a pharmaceutically effective carrier.

5. The pharmaceutical composition according to claim 4 further comprising a compound selected from one or more of the following classes of compounds:

diuretics; beta-adrenergic antagonists; alpha2-adrenergic agonists; alpha1-adrenergic antagonists; dual beta- and alpha-adrenergic antagonists; calcium channel blockers; potassium channel activators; anti-arrhythmics; ACE inhibitors; AT1 receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; CNS acting agents; calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endotheliin-converting enzyme (NEP/ECE) inhibitors; nociceptin receptor (ORL-1) agonists; xanthine oxidase inhibitors; benzodiazepine agonists; cardiac myosin activators; chymase inhibitors; endothelial nitric oxide synthase (ENOS) transcription enhancers; and neutral endopeptidase inhibitors.

6. A compound of formula Xa having the following structure:

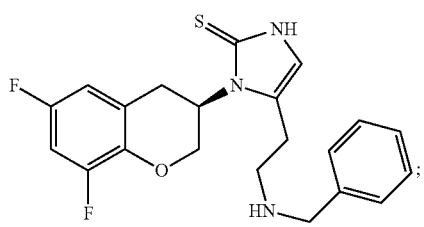

or a pharmaceutically acceptable salt thereof.

7. A pharmaceutical composition comprising a therapeutically effective amount of a compound according to claim 6, in combination with a pharmaceutically effective carrier.

8. The pharmaceutical composition according to claim 6 further comprising a compound selected from one or more of the following classes of compounds:

diuretics; beta-adrenergic antagonists; alpha2-adrenergic agonists; alpha 1-adrenergic antagonists; dual beta- and alpha-adrenergic antagonists; calcium channel blockers; potassium channel activators; anti-arrhythmics; ACE inhibitors; ATI receptor antagonists; renin inhibitors; lipid lowerers, vasopeptidase inhibitors; nitrates; endothelin antagonists; neutral endopeptidase inhibitors; anti-angiotensin vaccines; vasodilators; phosphodiesterase inhibitors; cardiac glycosides; serotonin antagonists; CNS acting agents; calcium sensitisers; HMG CoA reductase inhibitors; vasopressin antagonists; adenosine A1 receptor antagonists; atrial natriuretic peptide (ANP) agonists; chelating agents; corticotrophin-releasing factor receptor; glucagon-like peptide-1 agonists; sodium, potassium ATPase inhibitors; advanced glycosylation end-products (AGE) crosslink breakers; mixed neprilysin/endotheliin-converting enzyme (NEP/ECE) inhibitors; nociceptin receptor (ORL-1) agonists; xanthine oxidase inhibitors; benzodiazepine agonists; cardiac myosin activators; chymase inhibitors; endothelial nitric oxide synthase (ENOS) transcription enhancers; and neutral endopeptidase inhibitors.

9. The compound according to claim 6, wherein the pharmaceutically acceptable salt is a hydrochloride salt.

* * * * *

UNITED STATES PATENT AND TRADEMARK OFFICE
CERTIFICATE OF CORRECTION

| | | |
|---|---|---|
| PATENT NO. | : 8,481,582 B2 | Page 1 of 1 |
| APPLICATION NO. | : 12/599014 | |
| DATED | : July 9, 2013 | |
| INVENTOR(S) | : Patricio Manuel Vieira Araujo Soares Da Silva | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 585 days.

Signed and Sealed this
Twenty-sixth Day of November, 2013

Margaret A. Focarino
*Commissioner for Patents of the United States Patent and Trademark Office*